US011796401B2

(12) United States Patent
Chong et al.

(10) Patent No.: US 11,796,401 B2
(45) Date of Patent: Oct. 24, 2023

(54) TEXTILE PRESSURE SENSOR ARRAY AND PRESSURE DISTRIBUTION MAPPING SYSTEM

(71) Applicant: Nano and Advanced Materials Institute Limited, Hong Kong (HK)

(72) Inventors: Yam Chong, Hong Kong (HK); Tao Xu, Hong Kong (HK); Li Fu, Hong Kong (HK); Chenmin Liu, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 0 days.

(21) Appl. No.: 17/714,168

(22) Filed: Apr. 6, 2022

(65) Prior Publication Data

US 2022/0326099 A1 Oct. 13, 2022

Related U.S. Application Data

(60) Provisional application No. 63/171,659, filed on Apr. 7, 2021.

(51) Int. Cl.
*G01L 1/18* (2006.01)
(52) U.S. Cl.
CPC ..................... *G01L 1/18* (2013.01)
(58) Field of Classification Search
CPC ............ G01L 5/162; G01L 1/205; G01L 1/18
See application file for complete search history.

(56) References Cited

U.S. PATENT DOCUMENTS

| | | | | |
|---|---|---|---|---|
| 4,591,944 A | * | 5/1986 | Gravel | B25J 13/085 361/170 |
| 4,839,512 A | * | 6/1989 | Speck | G01L 1/146 901/33 |
| 5,225,959 A | * | 7/1993 | Stearns | G06F 3/0447 361/283.1 |
| 5,237,879 A | * | 8/1993 | Speeter | G01D 5/14 345/174 |
| 5,276,508 A | * | 1/1994 | Boisvert | H04N 5/148 348/E5.068 |

(Continued)

*Primary Examiner* — Tran M. Tran
(74) *Attorney, Agent, or Firm* — Idea Intellectual Limited; Margaret A. Burke; Sam T. Yip

(57) ABSTRACT

A pressure distribution mapping system includes a flexible M×N textile-based pressure sensor array. with first and second electrode textile layers and a piezoresistive fabric layer with a sheet resistance of at least 60 k-ohm/square positioned between the first and second electrode textile layers. Individual pressure sensors are formed by an intersection between a row electrically-conductive path and a column electrically-conductive path along with the portion of the piezoresistive layer positioned at the intersection. A measurement system measures the resistance of each pressure sensor of the pressure sensor array. The measurement system includes a reading module with first op-amps connected to each row and second op-amps connected to each column. Plural switches switch between pressure sensor-enabled and pressure sensor-disabled positions to minimize a bus line crosstalk effect during pressure sensor reading A processor scans each pressure sensor and generates a pressure distribution profile based on a measured resistance of each pressure sensor.

18 Claims, 13 Drawing Sheets

(56) References Cited

U.S. PATENT DOCUMENTS

| | | | | |
|---|---|---|---|---|
| 5,381,696 A * | 1/1995 | Ichinose | G01L 1/18 | 73/771 |
| 5,505,072 A * | 4/1996 | Oreper | G01L 1/205 | 702/116 |
| 5,509,078 A * | 4/1996 | Hiraoka | H03F 3/68 | 381/1 |
| 5,756,904 A * | 5/1998 | Oreper | A61C 19/05 | 73/862.046 |
| 6,369,804 B1 * | 4/2002 | Sandbach | H01H 3/141 | 178/18.05 |
| 6,492,980 B2 * | 12/2002 | Sandbach | G06F 3/011 | 178/18.05 |
| 6,853,306 B1 * | 2/2005 | Nitschke | G01L 1/205 | 340/665 |
| 7,049,830 B1 * | 5/2006 | Thinnes | G01L 1/205 | 324/691 |
| 7,703,342 B2 * | 4/2010 | Ogawa | G01L 1/205 | 73/862.046 |
| 7,825,814 B2 * | 11/2010 | Lokhorst | A61B 5/6892 | 340/575 |
| 7,861,605 B2 * | 1/2011 | Ogawa | G01L 5/164 | 73/862.69 |
| 7,926,365 B2 * | 4/2011 | Yeh | G06F 3/045 | 73/862.046 |
| 7,992,448 B2 * | 8/2011 | Shimazu | G01L 1/2293 | 73/777 |
| 8,800,386 B2 * | 8/2014 | Taylor | G01L 1/18 | 73/862.041 |
| 8,804,909 B2 * | 8/2014 | Rao | A61B 6/54 | 378/204 |
| 8,844,079 B2 * | 9/2014 | Skinner | A61G 7/05776 | 5/713 |
| 9,642,470 B2 * | 5/2017 | Taylor | A47C 27/082 | |
| 9,746,964 B2 * | 8/2017 | Rosenberg | G01L 1/205 | |
| 9,851,269 B2 * | 12/2017 | Ibrocevic | G01L 5/0076 | |
| 10,240,265 B2 * | 3/2019 | McMaster | D04B 1/14 | |
| 10,534,478 B2 * | 1/2020 | Rosenberg | G06F 3/0442 | |
| 10,761,637 B2 * | 9/2020 | Wang | G06F 3/04144 | |
| 10,859,449 B2 * | 12/2020 | Sasagawa | G01L 5/228 | |
| 11,112,317 B2 * | 9/2021 | Hart | F16P 3/148 | |
| 2013/0088247 A1 * | 4/2013 | Tseng | G01L 1/26 | 324/693 |
| 2022/0214387 A1 * | 7/2022 | Thompson | G01L 1/144 | |

* cited by examiner

TEXTILE PRESSURE SENSOR ARRAY AND PRESSURE DISTRIBUTION MAPPING SYSTEM

CROSS-REFERENCE TO RELATED APPLICATION

The present application claims domestic priority to U.S. Provisional Patent Application 63/171,659, filed 7 Apr. 2021, the disclosure of which is incorporated by reference herein.

FIELD OF THE INVENTION

The present invention relates to pressure mapping systems and, more particularly, to pressure mapping systems that include pressure sensor arrays having reduced crosstalk.

BACKGROUND

Pressure mapping depicts a pressure distribution caused by interaction of objects that make contact with one another. One field of pressure mapping is used to determine the pressure distribution between one or more parts of the human body and support surfaces such as beds, chairs, automobile seats, athletic equipment, and footwear. Other pressure mapping systems are used in industrial fields including manufacturing and packaging.

Traditional tactile sensors are rigid, bulky and can only be used for single point pressure monitoring. Thus, they are not suitable for applications that require thin and flexible form factors or that require pressure mapping capabilities. Another type of pressure sensor, typically printed on plastic foils such as PET and PI, is flexible and suitable for pressure mapping, but suffers from reliability issues when it is applied to soft surfaces such as chair mats and mattresses. The printed metal electrodes and pressure sensitive material readily cracks when the sensor array is twisted or flexed, especially when the sensor is placed on soft surface such as mat. Although the plastic foil substrate is flexible, it is difficult to make the foil conform to 3D objects with curved surfaces. Thus, there is a need in the art for improved pressure sensor arrays for pressure mapping systems that can be applied to soft and flexible surfaces such as cushions, beds, and footwear insoles. The present invention addresses this need.

SUMMARY OF THE INVENTION

In one aspect, the present invention provides a pressure mapping system that includes a flexible M×N textile-based pressure sensor array. The pressure sensor array includes a first electrode textile layer having M row electrically-conductive paths separated by insulating regions between adjacent row electrically-conductive paths with a ratio of a width of an insulating region to a width of a row conductive path being greater than two in order to minimize crosstalk between neighboring pressure sensors. The pressure sensor array further includes a second electrode textile layer having N column electrically-conductive paths separated by insulating regions between adjacent column electrically-conductive paths with a ratio of a width of an insulating region to a width of a column conductive path being greater than two in order to minimize crosstalk from neighboring pressure sensors.

A piezoresistive fabric layer is positioned between the first electrode textile layer and the second electrode textile layer. The piezoresistive fabric layer has an electrical characteristic in which resistance varies in response to applied physical forces and is a continuous piezoresistive fabric layer with a sheet resistance of at least 60 k-ohm/square in order to minimize the crosstalk between neighboring pressure sensors.

Individual pressure sensors are formed by an intersection between a row electrically-conductive path and a column electrically-conductive path along with the portion of the piezoresistive layer positioned at the intersection.

A measurement system measures the resistance of each pressure sensor of the pressure sensor array. The measurement system includes a reading module with first op-amps connected to each row and second op-amps connected to each column. Plural switches switch between pressure sensor-enabled and pressure sensor-disabled positions to minimize a bus line crosstalk effect during pressure sensor reading.

A processor is coupled to the measurement system for scanning each pressure sensor and generating a pressure distribution profile based on a measured resistance of each pressure sensor.

In a further aspect, a width of an M row electrically-conductive path is from 2 mm to 100 mm.

In a further aspect, a width of an M row electrically-conductive path is from 2 mm to 20 mm.

In a further aspect, a width of an M-row insulating region is from 4 mm to 200 mm.

In a further aspect, a width of an M-row insulating region is from 4 mm to 40 mm.

In a further aspect, the M row electrically-conductive paths and the N column electrically-conductive paths are formed from electrically conductive layers respectively formed on the first electrode textile layer and the second electrode textile layer.

In a further aspect, the M row electrically-conductive paths and the N column electrically-conductive paths are formed from electrically conductive yarns respectively woven into the first electrode textile layer and the second electrode textile layer.

In a further aspect, the piezoresistive fabric layer includes piezoresistive yarn or yarn coated with a piezoresistive material.

In a further aspect, the piezoresistive fabric layer has a sheet resistance of between 60 k-ohm/square and 1 M-ohm/square.

In a further aspect, the system includes a power regulating circuit for providing stable and noise-less power for the system along with a sensor array driving electronic circuit and a sensor array feedback electronic circuit.

In a further aspect, the processor is a microprocessor including an analog to digital converter and a plurality of multifunction pins.

In a further aspect, the system includes a transmitter for transmitting data measured from the pressure sensor array.

In a further aspect, the measurement system measures an electronic resistance variation from scanning the pressure sensors. The scanning including a sequential selection of a pair of row and column electrodes to form an electrically conductive area; the reading of pressure sensor resistance variation is obtained from the analog-to digital converter.

In a further aspect, the microprocessor is configured to provide constant voltage to electrodes in the first electrode textile layer including a lower voltage to unselected electrodes and a higher voltage to a selected electrode and minimize crosstalk by providing a common ground to pressure sensors.

In a further aspect, electrodes in the second electrode textile layer are connected to the analog to digital converter pins to sample feedback voltage and the analog to digital converter further includes a resistor for pressure sensor array resistive functionality matching.

In a further aspect, the system includes multiplexing circuitry for connecting plural electrodes to multifunction pins.

In a further aspect, the data transmitter is configured to transmit data over a universal serial bus (USB) cable connection, a Bluetooth wireless connection or a Wi-Fi wireless connection.

In a further aspect, the system includes a display for displaying images of pressure distributions representing different pressure levels.

DETAILED DESCRIPTION

Figure 1A:
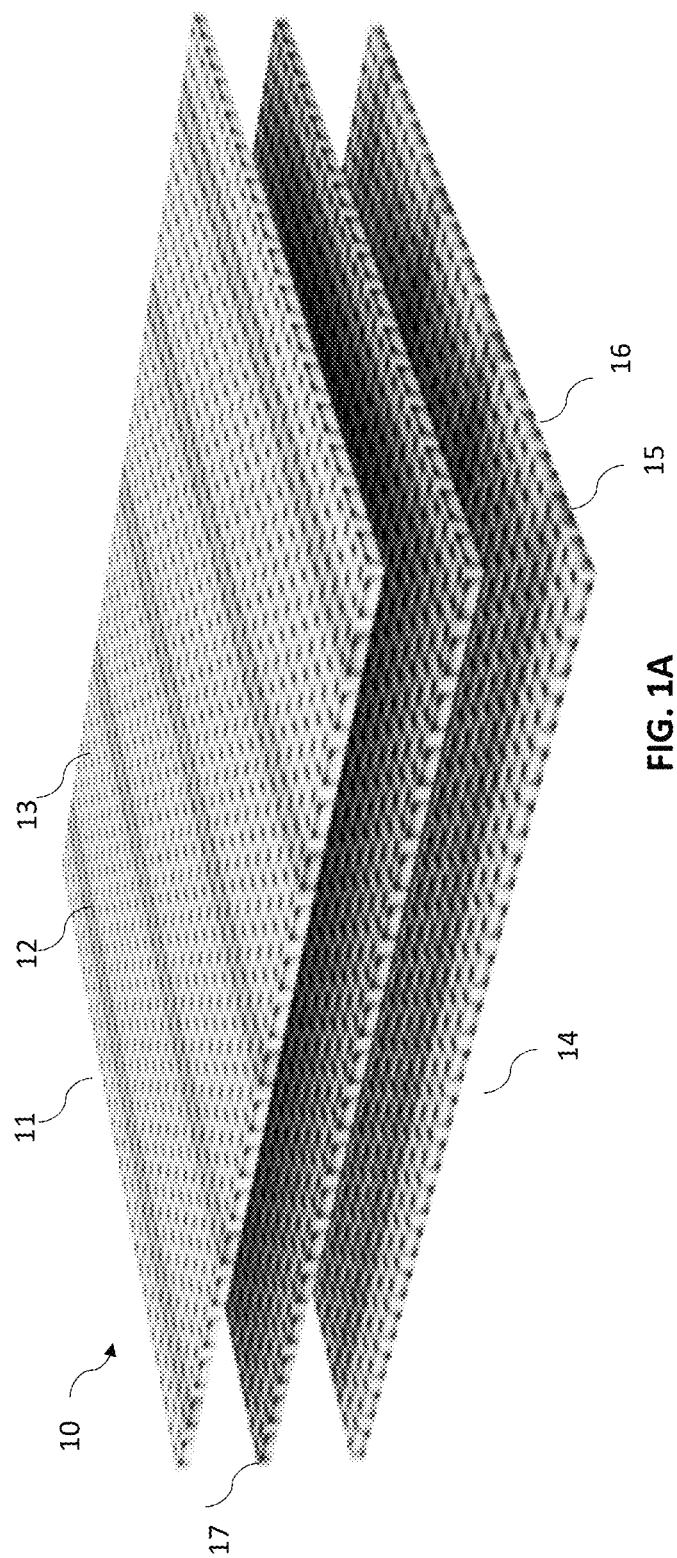
FIG. 1A illustrates a sensor array of an embodiment of the disclosure.

In order to solve the above-mentioned problems, it was determined that a textile-based pressure sensor array provides a flexible pressure mapping system that may be applied to soft substrates such as cushions, mattresses, and insoles. FIG. 1C depicts an overview of the pressure mapping system 100. In one embodiment, pressure mapping system 100 includes a flexible pressure sensor array 10, a measurement system for the array 20, a processor 30, a data transmitter 40, a sensory array feedback component 50, power regulation 60, and an optional display 70.

A flexible M×N pressure sensor array 10 is depicted in FIG. 1A. Textiles are ultra-flexible materials that may be fabricated in a variety of configurations to meet the system requirements. The pressure sensor array 10 includes a first upper electrode textile layer 11 having M row electrically-conductive paths 12 separated by insulating regions 13 between adjacent row electrically-conductive paths. A ratio of a width of an insulating region 13 to a width of a row conductive path 12 is greater than two in order to minimize crosstalk between neighboring pressure sensors. The pressure sensor array further includes a second electrode textile layer 14 having N column electrically-conductive paths 15 separated by insulating regions 16 between adjacent column electrically-conductive paths with a ratio of a width of an insulating region to a width of a column conductive path being greater than two in order to minimize crosstalk from neighboring pressure sensors.

A piezoresistive fabric layer 17 is positioned between the first electrode textile layer and the second electrode textile layer. The piezoresistive fabric layer has an electrical characteristic in which resistance varies in response to applied physical forces and is a continuous piezoresistive fabric layer with a sheet resistance of at least 60 k-ohm/square in order to minimize the crosstalk between neighboring pressure sensors. The sheet resistance may be from 60 k-ohm/square to 1 M-ohm/square or from 200 k-ohm/square to 1 M-ohm/square.

Individual pressure sensors/pixels are formed by an intersection between a row electrically-conductive path and a column electrically-conductive path along with the portion of the piezoresistive layer positioned at the intersection. In this manner, an M×N array of sensors is formed without the need for patterning and alignment of individual sensors, only rows and columns need to be formed. Using a piezoresistive fabric layer that spans the region between the electrode textile layers further simplifies construction of the sensor array in that there is no need to align individual piezoresistive elements with top and bottom electrodes, reducing the cost of the sensor array. However, since the activation of pressure sensors is through the row and column electrodes instead of individual pressure sensors, the configuration of FIG. 1A will result in crosstalk among neighboring pressure sensors in the same pressure sensor array. Therefore, the pressure mapping system includes several features that minimize the crosstalk in the pressure sensor array. These include the aforementioned ratio of insulating regions to conducting paths of at least 2; for example, a width of an M row electrically-conductive path or an N column electrically-conductive path may be from 2 mm to 100 mm, or from 2 mm to 20 mm. A width of an M-row insulating region may be from 4 mm to 200 mm (when the conducting path is from 2 mm to 100 mm) or from 4 mm to 40 mm (when the conducting path is from 2 mm to 20 mm)

Each electrode textile layer (11 or 14) may include woven or knitted textiles with conductive and insulating portions prepared with conductive yarn and non-conductive/insulating yarn respectively. The yarns/threads may themselves be conductive/insulating or conductors/insulators may be printed on the fabric. Examples of conductive yarns/threads include carbon/graphite-based yarns/threads, metal-based yarns/threads such as stainless-steel yarn and silver coated yarn. Examples of insulating yarns/threads include cellulose-based and polymer-based yarns/threads such as cotton, polyester, nylon, or lycra. Similarly, the piezoresistive layer 17 may be formed from piezoresistive yarns/threads such as carbon coated yarns or piezoresistive materials may be printed on the fabric with carbon ink. To reduce the resistance contribution from the conductive electrode bus line, the electrode textile layer (11 or 14) has much lower resistance than the piezoresistive layer. The measured sheet resistance of the electrode textile layer is normally less than 1% of the measured sheet resistance of the piezoresistive layer.

Figure 1B:
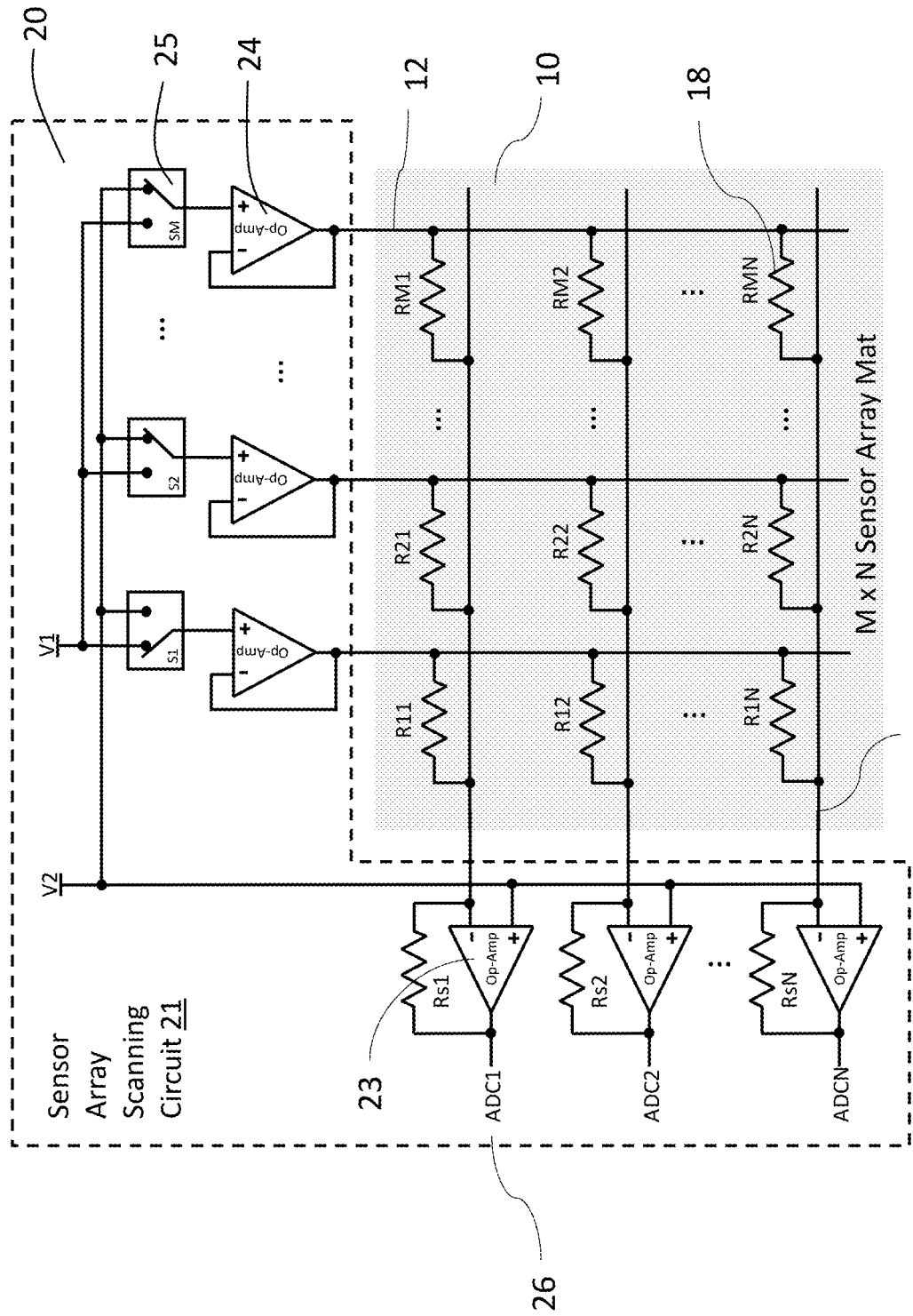
FIG. 1B illustrates the peripheral circuit for scanning a M×N textile sensor array of an embodiment of the disclosure.
Figure 1C:
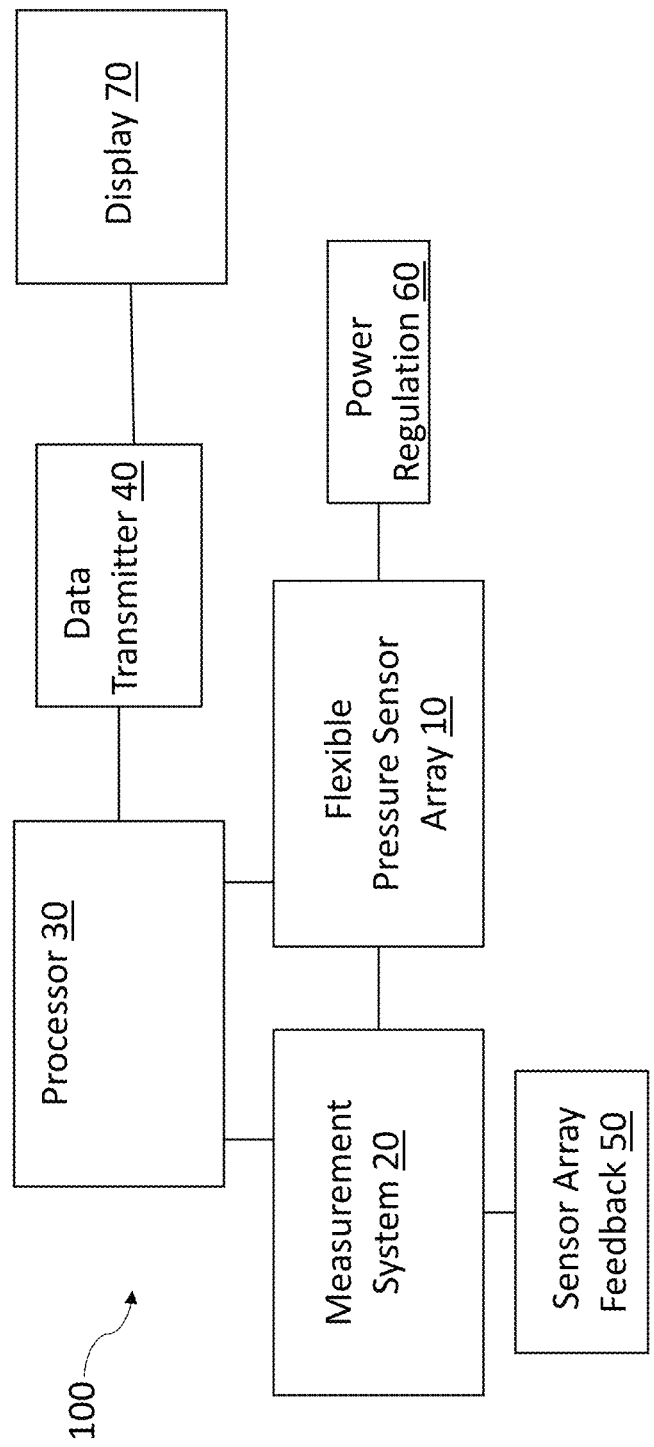
FIG. 1C is an overview of a pressure mapping system according to an embodiment.

To further reduce the effects of crosstalk, a measurement system 20 measures the resistance of each pressure sensor of the pressure sensor array. Further details of the measurement system are depicted in FIG. 1B. FIG. 1B shows an equivalent circuit for the M×N pressure sensor array 10 in which each sensor is modeled by a resistive element 18. The measurement system 20 includes a reading module (or scanning circuit 21) with first op-amps 23 connected to each row and second op-amps 24 connected to each column. Plural switches 25 switch between pressure sensor-enabled and pressure sensor-disabled positions to minimize a bus line crosstalk effect during pressure sensor reading.

The combination of a scanning circuit with op-amps, use of the selected sheet resistance of piezoresistive textile layer, and the pattern and spacing of the row and column electrodes separated by insulating regions achieves minimal crosstalk (<3%) resulting in an acceptable pressure mapping system performance. The discussion below describes in further detail the manner in which crosstalk is reduced in pressure mapping system 100.

EXAMPLES

Case 1:

The crosstalk effect can be one of the most challenging issues to be address in textile-based pressure sensor array and can be particularly pronounced given the continuous or unitary nature of a piezoresistive sensing layer and the row-column scanning method. Due to the unitary nature of a piezoresistive material layer and the close distances between neighboring sensors, active sensors within the same array can be mechanically and electrically coupled together to generate crosstalk effect while a force is applied spanning multiple sensors on the array. The scanning circuit 21 is based on a zero potential method with a high readout rate for suppressing the bus line crosstalk problem. It uses (M+N) wires, (M+N) op-amps, and N synchronous scanning channels in the pressure sensor array 10 with M×N sensors, keeping all scanning electrodes and all driving electrodes virtually at equipotential and reducing the bus line crosstalk sufficiently.

The circuit 21 inside the dotted line section in FIG. 1B is a sensor array scanning circuit for scanning the M×N pressure sensor array. Each resistor 18 in the equivalent circuit of the M×N pressure sensor array represents the resistance of the corresponding pressure sensor located at the intersection of an $M^{th}$ row electrodes and an $N^{th}$ column electrode. V1 may be set to a higher voltage, e.g. 4V, and V2 may be set to a lower voltage, e.g. 3V. Since both input pins' voltage of the op-amp are positive, the op-amp can connect to 5V and ground as the positive supply and negative supply, which simplifies the circuit design and eliminates possible noise from a negative voltage supply circuit.

Each horizontal row electrically-conductive path 15 on the bottom layer of the sensor array may be configured to act as a scanning electrode and connected to an analog-to-digital converter 26 (ADC) via an inverting operation amplifier 23. Each vertical column electrically-conductive path 12 on the top layer of the sensor array may be configured to act as a driving electrode and connected to voltage supply V1 and V2 via a unity gain operation amplifier (op-amp) 24 and an analog switch 25. The analog switches 25 operates in conjunction with adjacent switches to selectively activate each individual specific pressure sensors. A switch selects V1 to enable the sensor to which it is connected, or selects V2 to disable the sensor to which it is connected. The scanning sequence is synchronized by processor 30 which has multiple ADC pins and multiple general purpose output pins. The scanning sequence is column by column, each time scanning all the sensors on the same column at the same time.

In a further aspect, electrodes in the second electrode textile layer are connected to the analog to digital converter pins to sample feedback voltage and the analog to digital converter 26 further communicates with a resistor Rs1 for pressure sensor array resistive functionality matching.

Figure 2:
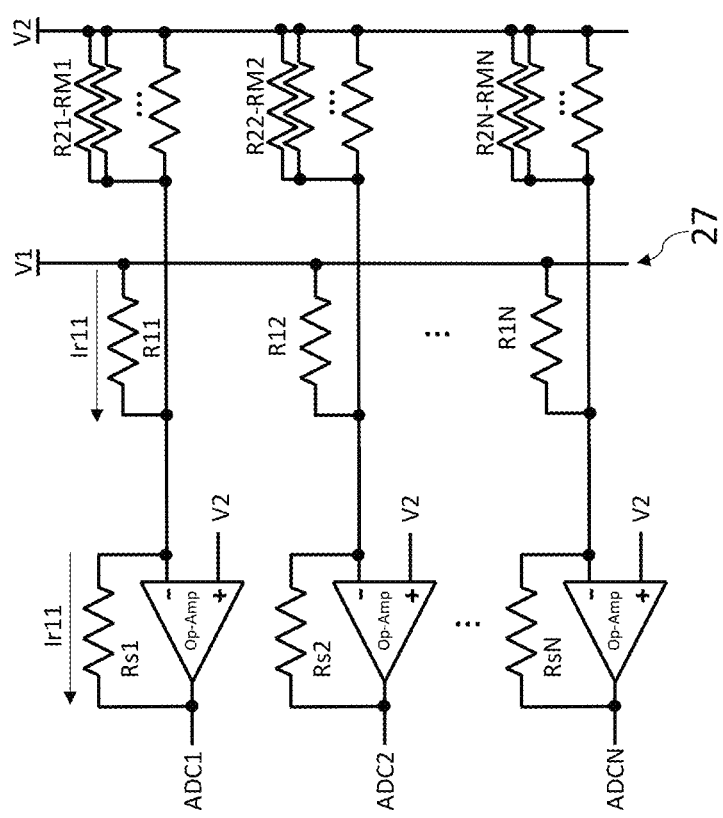
FIG. 2 illustrates the equivalent circuit model of scanning column 1 sensors of an embodiment of the disclosure.

FIG. 2 shows an example, when switch S1 of FIG. 1B is switched to V1 and the other switches, S2 to SM, are switched to V2. In this position, all of the sensors in column 1 (element 27) are activated and all the other sensors are deactivated. The virtual equipotential appearing at the two inputs of the op-amp 24 on every driving electrode keeps the scanning electrode at the set voltage V1 and all the other scanning electrodes at V2 potential. The virtual equipotential appearing at the two inputs of the op-amp 23 on every scanning electrode also kept each scanning electrode at V2 potential. Therefore, the two terminals of each deactivated sensor had equal potential and no bypass current existed on the deactivated sensors.

As shown in FIG. 2, by using an op-amp on every scanning electrode and driving electrode, the bypass effect of the equivalent adjacent column scanning sensors and row adjacent deactivated sensors was eliminated. Thus, the crosstalk caused by the column conductive path and row conductive path was suppressed.

Figure 3A:
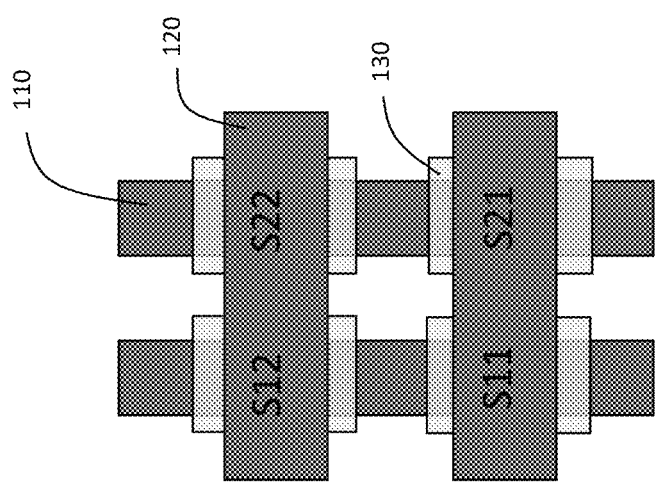
FIG. 3A illustrates a 2×2 sensor array layout of a comparative embodiment (discrete piezoresistive material).

To evaluate the performance of the above circuit, a 5×5 sensor array was constructed, with each conductive path having a width of 3 mm and the insulating region between adjacent conductive paths was 15 mm; the typical surface resistance of the piezoresistive material layer was 200K ohm. FIG. 3A shows the layering of the sensor array, the top and bottom layer is the row and column electrodes (110, 120 in FIG. 3A). The middle layer is the piezoresistive material layer (130 in FIG. 3A). The piezoresistive material block for sensors is isolated with each other to eliminate row-to-row resistance and column-to-column resistance. A 100 g weight was put on sensor S22 as a control before evaluation started. The processor 30 caused the measurement system 20 to read out and record the ADC value of sensor S22; during the evaluation a varying weight was placed on each neighboring sensor in sequency to evaluate the impact on the measurement for control sensor S22.

Figure 3B:
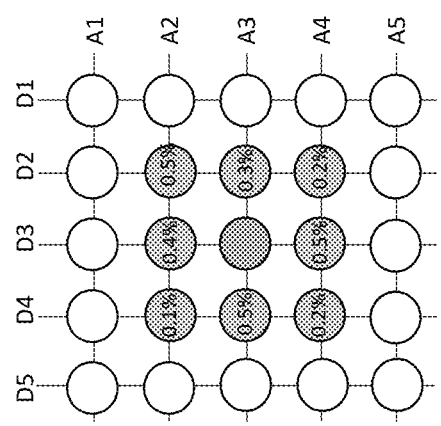
FIG. 3B illustrates crosstalk effect of an embodiment of the disclosure.

For the sensor array shown in FIG. 3A, both neighboring row sensors and neighboring column sensors had some effect on sensor S22 errors, but the effect is very small and the resultant error is less than 0.5%. Note that this value includes circuit board noise and mechanical vibration when applying force onto neighboring sensor. FIG. 3B depicts the maximum crosstalk effect of each of the neighboring sensors. The maximum crosstalk effect was 0.5%, demonstrating that the scanning circuit of measurement system 20 is effective in minimizing the crosstalk due to neighboring sensors on the sensor array.

Figure 4:
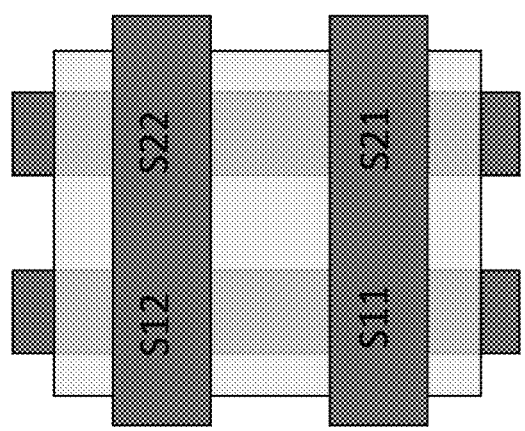
FIG. 4 illustrates a 2×2 sensor array layout of an embodiment of the disclosure (unitary piezoresistive material).
Figure 5A:
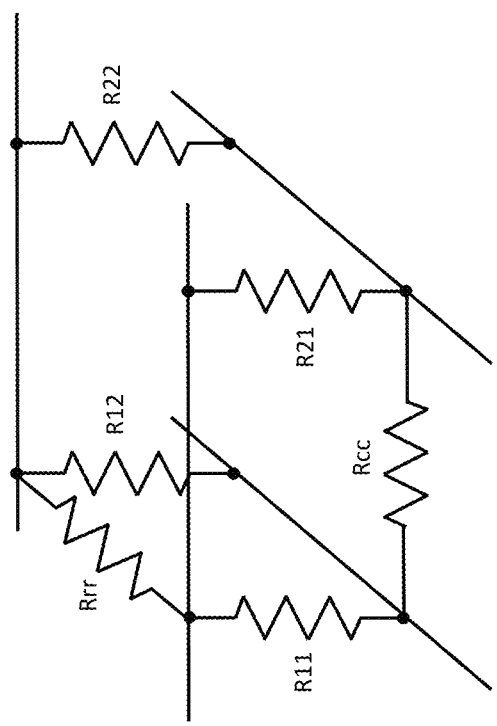
FIG. 5A illustrates parasitic paths of R11 of an embodiment of the disclosure.
Figure 5B:
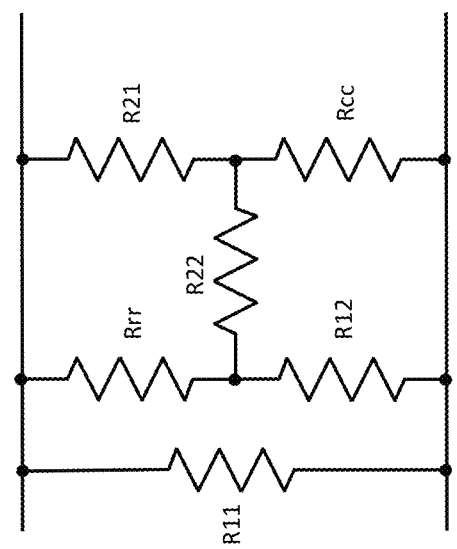
FIG. 5B illustrates an equivalent circuit of reading R11 of an embodiment of the disclosure.
Figure 5C:
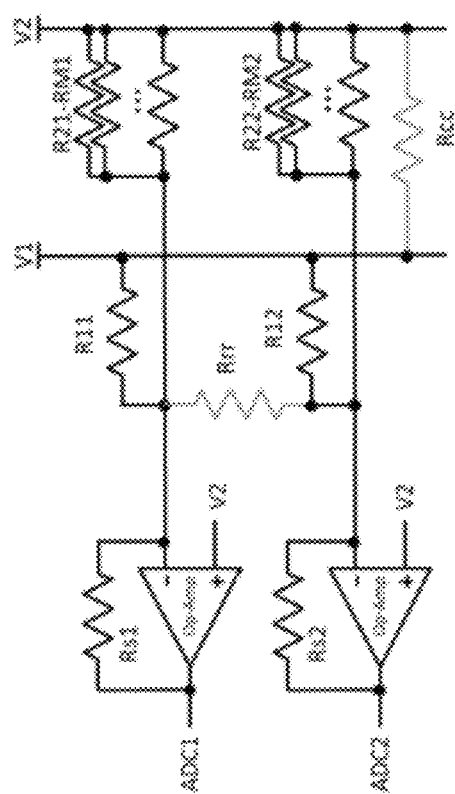
FIG. 5C illustrates an equivalent circuit with op-amp driving and scanning scheme of an embodiment of the disclosure.

Case 2:

In this case, as shown in FIG. 4, the middle layer is a unitary piezoresistive material which is connected for all sensors on the same array; as discussed above, using a unitary piezoresistive layer both simplifies the manufacturing and reduces the cost of the sensor array. The remaining features of the sensor array and the scanning circuit is the same as for case 1. When scanning the resistance value (as altered by an applied pressure) of each sensor, there are multiple parasitic paths of different lengths and resistance (FIGS. 5A-5C), such as the bulk conductivity of the piezoresistive material layer, modeled as parasitic resistances Rcc (column to column) and Rrr (row to row). These parasitic resistances cause errors in the reading of voltages and affect the reading of the sensor output signal.

In order to eliminate this crosstalk effect, the in-plane resistance of the piezoresistive material sheet must be significantly larger than the through-plane resistance. There are two ways to increase the in-plane resistance, either by increasing the spacing between conductive paths, or increasing the material surface resistance. For spacing control on the electrode textile layer, the ratio between the width of insulating region and the width of conductive paths was optimized to greater than 2 to minimize the crosstalk effect. The sheet resistance of the piezoresistive material was investigated within a range of 60K to 200K to minimize sensor crosstalk. Sheet resistance larger than 200 k is possible for sensor array fabrication, but it may have uniformity problem due to the large variation of resistivity for the piezoresistive sensing material when the bulk resistance is extremely high. Although neighboring resistors are eliminated in the op-amp driving and scanning circuit of the measurement system, Rrr and Rcc still affect the reading accuracy of an individual sensor when a unitary piezoresistive material layer is implemented in the sensor array. When the resistance is lower, the op-amps are more stressed. The previous circuitry proposed eliminates the crosstalk by interposing an unity gain amplifier on every column and an inverting amplifier on every row. In this way, a difference of potential which must be as close as possible to zero is imposed across the sensors not read, thus counteracting the effect of the parasitic paths, and also of resistances Rrr and Rcc.

Figure 6:
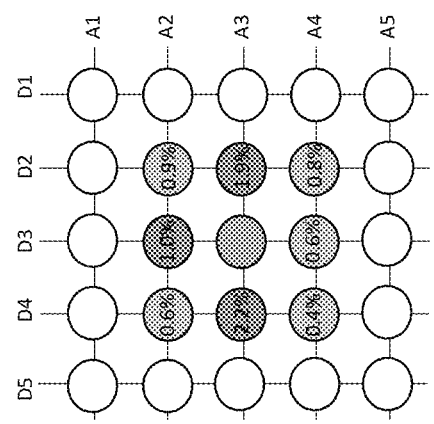
FIG. 6 illustrates crosstalk effect error of S22 on varying neighboring sensors of an embodiment of the disclosure.

FIG. 6 shows the evaluation result of the crosstalk effect at control sensor S22 when varying force applied to its neighboring sensors on a sensor array with a unitary piezoresistive material layer. The sensor array mat was a 5×5 array, electrode width was 3 mm, spacing of electrodes were 15 mm, the typical surface resistance of the piezoresistive material was 200K ohm/square. Compared to the sensor array of case 1 (comparative example) with discrete piezoresistive material portions for each sensor as shown in FIGS. 3A-3B, higher error values are observed for the sensor array using the unitary piezoresistive material layer. The maximum error was 2.2% as shown in FIG. 6.

Figure 7:
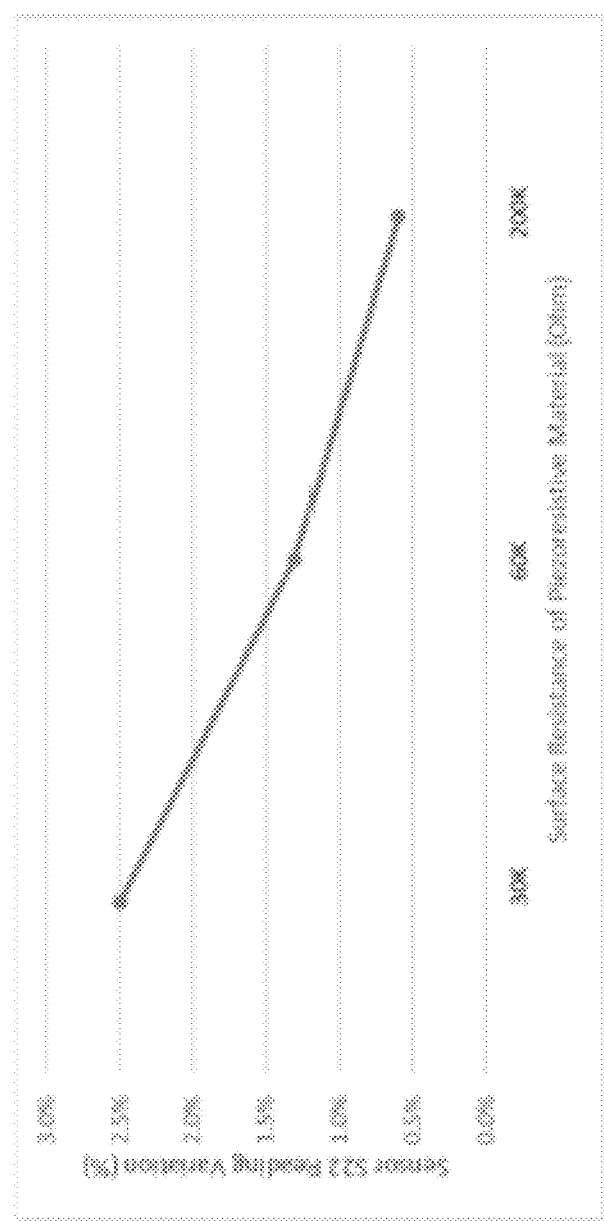
FIG. 7 illustrates average crosstalk errors of different piezoresistive materials of an embodiment of the disclosure (electrode width and spacing ratio=1:4).

Since the sheet resistance of the piezoresistive material layer will affect the value of Rrr and Rcc, it will also impact the error of the sensor reading. FIG. 7 shows the relationship between the sheet resistance of piezoresistive material and the average reading error of sensors. A sheet resistance of >60 k-ohm was determined to be sufficient to minimize the crosstalk of sensors and improve reading accuracy.

Figure 8:
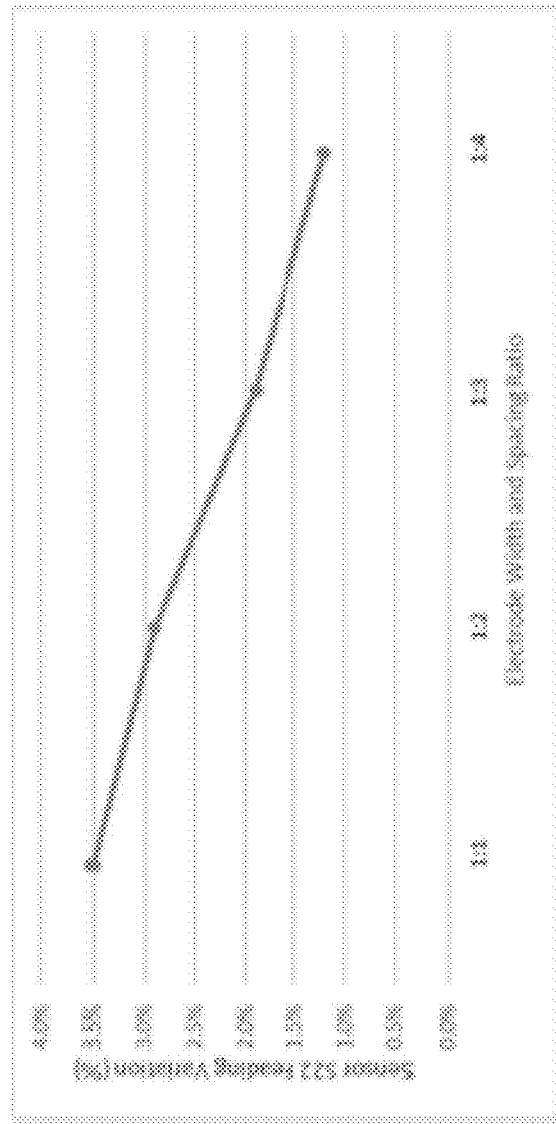
FIG. 8 illustrates average crosstalk errors of sensor array with different electrode spacing ratio of an embodiment of the disclosure (piezoresistive material resistance=60 k-ohm).

Another parameter that affects the reading error of sensors is the design pattern of the row and column electrodes, more specifically the width ratio between the insulating region and the conductive paths. FIG. 8 shows the evaluation result of crosstalk effect for different ratios between the width of the insulating region and the width of conductive paths. It was found that the crosstalk effect decreases when the ratio increases. Ratio increases that mean the distance between adjacent electrodes increases, so that Rcc and Rrr are increased. The crosstalk effect of these two resistances to the circuit are decreased. It also demonstrates that a width ratio of greater than 2 for the insulating region and the conductive paths of the row and column electrodes provides an adequate accuracy for the sensor array.

In summary, the present invention has the following characteristics:
1) The textile-based pressure sensor array is ultra-flexible and conforms to 3D surfaces for pressure monitoring; pressure distribution may be displayed through M×N sensor grids. The column and row structured electrodes sheets are woven or knitted for easy manufacturing and possess good reliability during usage. The piezoresistive sensing material of the sensor array is a unitary layer without any pattern for easy manufacturing and low-cost fabrication.
2) A device for measuring resistance of each sensor on the sensor array through scanning circuit built with op-amps to minimize bus line crosstalk effect during sensor reading with row-column method. The crosstalk of the neighboring sensors is reduced to <3%.
3) High sensor signal accuracy can be achieved through the reduction of crosstalk by using piezoresistive sensing material with high sheet resistance, e.g., >60K-Ω/square.
4) High sensor signal accuracy can be achieved through the reduction of crosstalk by using the width ratio of greater than 2 for the insulating and conductive portions of the row and column electrode textile layers.

As used herein, terms "approximately", "basically", "substantially", and "about" are used for describing and explaining a small variation. When being used in combination with an event or circumstance, the term may refer to a case in which the event or circumstance occurs precisely, and a case in which the event or circumstance occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all the ranges disclosed in the present disclosure include endpoints. The term "substantially coplanar" may refer to two surfaces within a few micrometers (μm) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

Several embodiments of the present disclosure and features of details are briefly described above. The embodiments described in the present disclosure may be easily used as a basis for designing or modifying other processes and structures for realizing the same or similar objectives and/or obtaining the same or similar advantages introduced in the embodiments of the present disclosure. Such equivalent construction does not depart from the spirit and scope of the present disclosure, and various variations, replacements, and modifications can be made without departing from the spirit and scope of the present disclosure.

The invention claimed is:

1. A pressure distribution mapping system comprising:
a flexible M×N textile-based pressure sensor array having:
a first electrode textile layer having M row electrically-conductive paths separated by insulating regions between adjacent row electrically-conductive paths with a ratio of a width of an insulating region to a width of a row conductive path being greater than two in order to minimize crosstalk between neighboring pressure sensors;

a second electrode textile layer having N column electrically-conductive paths separated by insulating regions between adjacent column electrically-conductive paths with a ratio of a width of an insulating region to a width of a column conductive path being greater than two in order to minimize crosstalk from neighboring pressure sensors;

a piezoresistive fabric layer positioned between the first electrode textile layer and the second electrode textile layer, the piezoresistive fabric layer having an electrical characteristic in which resistance varies in response to applied physical forces, the piezoresistive fabric layer being a continuous piezoresistive fabric layer with a sheet resistance of at least 60 k-ohm/square to minimize the crosstalk between neighboring pressure sensors;

wherein an individual pressure sensor is formed by an intersection between a row electrically-conductive path and a column electrically-conductive path and a portion of the piezoresistive layer positioned at the intersection;

a measurement system for measuring a resistance of each pressure sensor of the pressure sensor array, the measurement system including a reading module including a voltage supply V1 and a voltage supply V2, first op-amps connected to each row and second op-amps connected to each column and a plurality of switches for switching between pressure sensor-enabled and pressure sensor-disabled positions during pressure sensor readings with a first column switch connecting one of the first op-amps to the first voltage V1 while remaining column switches connect remaining first op-amps to the second voltage to V2 such that two terminals of each deactivated pressure sensor have equal potential and bypass current does not flow through the deactivated pressure sensors in order to minimize a bus line crosstalk effect during pressure sensor reading; and a processor coupled to the measurement system for scanning each pressure sensor and generating a pressure distribution profile based on a measured resistance of each pressure sensor.

2. The pressure distribution mapping system of claim 1, wherein a width of a row or a column electrically-conductive path is from 2 mm to 100 mm.

3. The pressure distribution mapping system of claim 1, wherein a width of a row or a column electrically-conductive path is from 2 mm to 20 mm.

4. The pressure distribution mapping system of claim 2, wherein a width of a row or a column insulating region is from 4 mm to 200 mm.

5. The pressure distribution mapping system of claim 3, wherein a width of a row or a column insulating region is from 4 mm to 40 mm.

6. The pressure distribution mapping system of claim 1, wherein the M row electrically-conductive paths and the N column electrically-conductive paths are formed from electrically conductive layers respectively formed on the first electrode textile layer and the second electrode textile layer.

7. The pressure distribution mapping system of claim 1, wherein the M row electrically-conductive paths and the N column electrically-conductive paths are formed from electrically conductive yarns respectively woven into the first electrode textile layer and the second electrode textile layer.

8. The pressure distribution mapping system of claim 1, wherein the piezoresistive fabric layer comprises piezoresistive yarn or yarn coated with a piezoresistive material.

9. The pressure distribution mapping system of claim 1, wherein piezoresistive fabric layer has a sheet resistance of between 60 k-ohm/square and 1M-ohm/square.

10. The pressure distribution mapping system of claim 1, further comprising:
a power regulating circuit for providing stable and noise-less power for the system;
a sensor array driving electronic circuit; and
a sensor array feedback component.

11. The pressure distribution mapping system of claim 10, wherein the processor is a microprocessor including an analog to digital converter and a plurality of multifunction pins.

12. The pressure distribution mapping system of claim 11, further comprising a transmitter for transmitting data measured from the pressure sensor array.

13. The pressure distribution mapping system of claim 12, wherein the measurement system measures an electronic resistance variation from scanning the pressure sensors, the scanning including a sequential selection of a pair of row and column electrodes to form an electrically conductive area, the reading of pressure sensor resistance variation being obtained from the analog-to digital converter.

14. The pressure distribution mapping system of claim 12, wherein the microprocessor is configured to provide constant voltage to electrodes in the first electrode textile layer including a lower voltage to unselected electrodes and a higher voltage to a selected electrode and minimize crosstalk by providing a common ground to the pressure sensors.

15. The pressure distribution mapping system of claim 12, wherein electrodes in the second electrode textile layer are connected to the analog to digital converter pins to sample feedback voltage, the analog to digital converter further communicating with a resistor for pressure sensor array resistive functionality matching.

16. The pressure distribution mapping system of claim 15, further comprising multiplexing circuitry for connecting plural electrodes to multifunction pins.

17. The pressure distribution mapping system of claim 12, wherein the transmitter is configured to transmit data over a universal serial bus (USB) cable connection, a Bluetooth wireless connection or a Wi-Fi wireless connection.

18. The pressure distribution mapping system of claim 12 further comprising a display for displaying images of pressure distributions representing different pressure levels.

* * * * *